(12) United States Patent
Waechter-Stehle et al.

(10) Patent No.: US 10,729,406 B2
(45) Date of Patent: Aug. 4, 2020

(54) ULTRASONIC DIAGNOSIS OF CARDIAC PERFORMANCE USING HEART MODEL CHAMBER SEGMENTATION WITH USER CONTROL

(71) Applicant: KONINKLIJKE PHILIPS N.V., Eindhoven (NL)

(72) Inventors: Irina Waechter-Stehle, Eindhoven (NL); Frank Michael Weber, Eindhoven (NL); Christian Buerger, Eindhoven (NL); Robert Joseph Schneider, Eindhoven (NL); David Prater, Eindhoven (NL); Scott Holland Settlemier, Eindhoven (NL); Michael Daniel Cardinale, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 179 days.

(21) Appl. No.: 15/556,331

(22) PCT Filed: Mar. 1, 2016

(86) PCT No.: PCT/EP2016/054255
§ 371 (c)(1),
(2) Date: Sep. 7, 2017

(87) PCT Pub. No.: WO2016/142204
PCT Pub. Date: Sep. 15, 2016

(65) Prior Publication Data
US 2018/0161009 A1   Jun. 14, 2018

Related U.S. Application Data

(60) Provisional application No. 62/130,787, filed on Mar. 10, 2015, provisional application No. 62/130,805, filed on Mar. 10, 2015.

(30) Foreign Application Priority Data

Mar. 30, 2015   (EP) ..................... 15161561

(51) Int. Cl.
*G06K 9/00*       (2006.01)
*A61B 8/00*       (2006.01)
(Continued)

(52) U.S. Cl.
CPC ............ *A61B 8/465* (2013.01); *A61B 8/0883* (2013.01); *A61B 8/483* (2013.01); *A61B 8/5223* (2013.01);
(Continued)

(58) Field of Classification Search
None
See application file for complete search history.

(56) References Cited

U.S. PATENT DOCUMENTS 5,474,073 A   12/1995   Schwartz
5,485,842 A   1/1996   Quistgaard
(Continued)

FOREIGN PATENT DOCUMENTS

JP   2010259656 A   11/2010
WO   2014195237 A1   12/2014

OTHER PUBLICATIONS

Dias et al "Wall Positioning and Thickness Estimation From Sequences of Echocardiographic Images" IEEE Transactions on Medical Imaging, vol. 15, No. 1, Feb. 2, 1996.

*Primary Examiner* — Wei Wen Yang

(57) ABSTRACT

An ultrasonic diagnostic imaging system has a user control by which a user positions the user's selection of a heart chamber border in relation to two myocardial boundaries identified by a deformable heart model. The user's border is positioned by a single degree of freedom control which positions the border as a function of a single user-determined
(Continued)

value. This overcomes the vagaries of machine-drawn borders and their mixed acceptance by clinicians, who can now create repeatably-drawn borders and exchange the control value for use by others to obtain the same results.

19 Claims, 8 Drawing Sheets

(51) Int. Cl.
  *A61B 8/08* (2006.01)
  *G06T 7/149* (2017.01)
  *G06T 7/12* (2017.01)
  *G06T 7/00* (2017.01)
(52) U.S. Cl.
  CPC ............ *A61B 8/543* (2013.01); *G06T 7/0012* (2013.01); *G06T 7/12* (2017.01); *G06T 7/149* (2017.01); *A61B 8/467* (2013.01); *G06T 2207/10132* (2013.01); *G06T 2207/30048* (2013.01)

(56) References Cited

U.S. PATENT DOCUMENTS

| | | |
|---|---|---|
| 5,601,084 A | 2/1997 | Sheehan et al. |
| 5,720,291 A | 2/1998 | Schwartz |
| 5,833,613 A | 11/1998 | Averkiou et al. |
| 6,013,032 A | 1/2000 | Savord |
| 6,186,950 B1 | 2/2001 | Averkiou et al. |
| 6,375,617 B1 | 4/2002 | Fraser |
| 6,491,636 B2 | 12/2002 | Chenal et al. |
| 6,692,438 B2 | 2/2004 | Skyba et al. |
| 2004/0267125 A1* | 12/2004 | Skyba ................ A61B 8/0858 600/443 |
| 2005/0075567 A1 | 4/2005 | Skyba et al. |
| 2007/0055161 A1 | 3/2007 | Garg et al. |
| 2009/0136109 A1 | 5/2009 | Salgo et al. |
| 2012/0078097 A1 | 3/2012 | Wang et al. |
| 2015/0294082 A1* | 10/2015 | Passerini ................ G16H 50/50 703/11 |
| 2015/0371437 A1* | 12/2015 | Mansi .................... G06T 11/60 382/131 |

\* cited by examiner

ULTRASONIC DIAGNOSIS OF CARDIAC PERFORMANCE USING HEART MODEL CHAMBER SEGMENTATION WITH USER CONTROL

This application is the U.S. National Phase application under 35 U.S.C. § 371 of International Application No. PCT/EP2016/054255, filed on Mar. 1, 2016, which claims the benefit of U.S. Provisional Application Ser. No. 62/130, 787, filed Mar. 10, 2015; U.S. Provisional Application Ser. No. 62/130,805 filed Mar. 10, 2015 and EP 15161561.4 filed Mar. 30, 2015. These applications are hereby incorporated by reference herein.

This invention relates to medical diagnostic ultrasound systems and, in particular, to the use of a heart model to segment myocardial boundaries with user control to identify a heart chamber border.

Ultrasonic imaging is routinely used to diagnose cardiac performance by measurement of parameters such as ejection fraction and cardiac output. Such measurements require the volume of blood in a heart chamber at various phases of the heart cycle to be delineated in two or three dimensional images of a heart chamber. Typically measurements of the volume of cardiac chambers, such as the left ventricle, have been generated by users hand tracing the endocardial boundary of the chamber. Such tracings are subject to significant variability due to differences in the criteria different users utilize in determining where to locate the tracing. Automatic methods have been developed to attempt to automate this boundary tracing, such as the automated border tracing methodology described in U.S. Pat. No. 6,491,636 (Chenal et al.) In this technique, anatomical landmarks of a chamber are located, including the mitral valve plane corners and the apex of the heart chamber. One of a plurality of standard, expert-validated endocardial shapes are then fit to these landmarks. The automatically drawn border can then be manually adjusted by rubberbanding, by which the user moves control points on the border to adjust its final position over the endocardium. This processing is done for images taken at the end systole and end diastole heart phases. The two borders can be compared or subtracted to estimate ejection fraction or cardiac output. For example, US 2009/0136109 discloses to produce a myocardium thickness volume by comparing the identified endocardial border (which defines an inner surface of the myocardium) and the identified epicardial border (which defines an outer surface of the myocardium). The myocardium thickness volume of US 2009/0136109 is hollow, with the hollow space inside being the volume of the heart chamber. Ejection fraction can be estimated by well-established methods such as an automated Simpson's algorithm (rule of disks), to measure the fraction of the chamber volume ejected with each contraction of the heart.

But automated image analysis methods do not always produce heart chamber delineations that are acceptable to all users. This lack of success is due in large part to the inability of the automatic methods to consistently locate the border where any given user believes the border should be placed. Much of this poor performance is due to variations between different users on what are the anatomical landmarks which specify where the true border lies.

It is an object of the present invention to provide users with a simple automated tool for delineating the location of an acceptable heart chamber border. It is a further object to do this by use of an automated deformable heart model which is able to locate multiple myocardial boundaries. It is a further object that such delineations be standardized, and capable of comparison and the production of repeatable results among different users. Such results summarize the approach of one clinician into a single value that can be understood and communicated to other clinicians who have the same tool.

In accordance with the principles of the present invention, a diagnostic ultrasound system and method are described which diagnose cardiac performance. Images of a chamber of the heart are acquired and an image is segmented by use of a deformable heart model which is designed to delineate both an inner and an outer boundary of the myocardium, or alternatively several (3+) boundaries of the myocardium. A user control is provided which enables a user to define the user's preferred chamber border location in relation to one, both, or several of the segmented boundaries. The user control provides a single value, a single degree of freedom, which the user varies to locate the border, such as a percentage of the distance relative to the segmented boundaries. The single value can be shared with other users of the same tool, enabling other users to obtain the same results with other images, and hence a standardization of cardiac chamber border identification.

Figure 1:
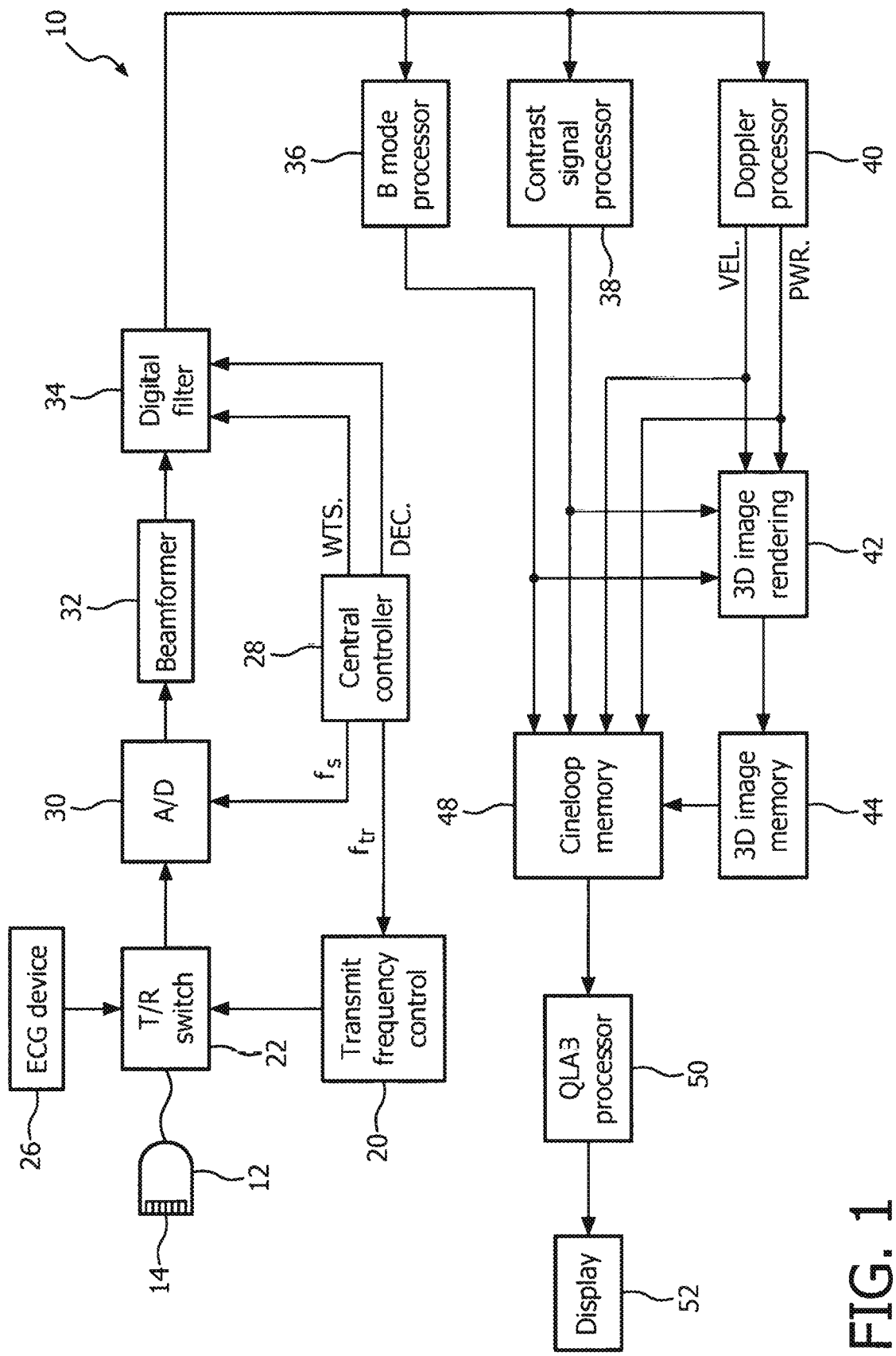
FIG. 1 illustrates in block diagram form an ultrasonic diagnostic imaging system constructed in accordance with the principles of the present invention.

Referring first to FIG. 1 an ultrasonic diagnostic imaging system 10 constructed in accordance with the principles of the present invention is shown in block diagram form. An ultrasonic probe 12 includes an array 14 of ultrasonic transducers that transmit and receive ultrasonic pulses. The array may be a one dimensional linear or curved array for two dimensional imaging, or may be a two dimensional matrix of transducer elements for electronic beam steering in three dimensions. The ultrasonic transducers in the array 14 transmit ultrasonic energy and receive echoes returned in response to this transmission. A transmit frequency control circuit 20 controls the transmission of ultrasonic energy at a desired frequency or band of frequencies through a transmit/receive ("T/R") switch 22 coupled to the ultrasonic transducers in the array 14. The times at which the transducer array is activated to transmit signals may be synchronized to an internal system clock (not shown), or may be synchronized to a bodily function such as the heart cycle, for which a heart cycle waveform is provided by an ECG device 26. When the heartbeat is at the desired phase of its cycle as determined by the waveform provided by ECG device 26, the probe is commanded to acquire an ultrasonic image. This enables acquisition at the end diastole and end systole heart phases, for instance. The frequency and bandwidth of the ultrasonic energy generated by the transmit frequency control circuit 20 is controlled by a control signal $f_{tr}$ generated by a central controller 28.

Echoes from the transmitted ultrasonic energy are received by the transducers in the array 14, which generate echo signals that are coupled through the T/R switch 22 and digitized by analog to digital ("A/D") converters 30 when the system uses a digital beamformer. Analog beamformers may also be used. The A/D converters 30 sample the received echo signals at a sampling frequency controlled by a signal $f_s$ generated by the central controller 28. The desired sampling rate dictated by sampling theory is at least twice the highest frequency of the received passband, and might be on the order of 30-40 MHz. Sampling rates higher than the minimum requirement are also desirable.

The echo signal samples from the individual transducers in the array 14 are delayed and summed by a beamformer 32 to form coherent echo signals. For 3D imaging with a two dimensional array, it is preferable to partition the beamformer between a microbeamformer located in the probe and the main beamformer in the system mainframe as described in U.S. Pat. No. 6,013,032 (Savord) and U.S. Pat. No. 6,375,617 (Fraser). The digital coherent echo signals are then filtered by a digital filter 34. In the illustrated ultrasound system, the transmit frequency and the receiver frequency are individually controlled so that the beamformer 32 is free to receive a band of frequencies which is different from that of the transmitted band such as a harmonic frequency band. The digital filter 34 bandpass filters the signals, and can also shift the frequency band to a lower or baseband frequency range. The digital filter can be a filter of the type disclosed in U.S. Pat. No. 5,833,613, for example. Filtered echo signals from tissue are coupled from the digital filter 34 to a B mode processor 36 for conventional B mode image processing.

Filtered echo signals of a contrast agent, such as microbubbles, are coupled to a contrast signal processor 38. Contrast agents are often used to more clearly delineate the endocardial wall in relation to contrast agent in the blood pool of the heart chamber, or to perform perfusion studies of the microvasculature of the myocardium as described in U.S. Pat. No. 6,692,438 for example. The contrast signal processor 38 preferably separates echoes returned from harmonic contrast agents by the pulse inversion technique, in which echoes resulting from the transmission of multiple differently modulated pulses to an image location are combined to cancel fundamental signal components and enhance harmonic signal components. A preferred pulse inversion technique is described in U.S. Pat. No. 6,186,950, for instance.

The filtered echo signals from the digital filter 34 are also coupled to a Doppler processor 40 for conventional Doppler processing to produce velocity and power Doppler signals. The output signals from these processors may be displayed as planar images, and are also coupled to a 3D image processor 42 for the rendering of three dimensional images, which are stored in a 3D image memory 44. Three dimensional rendering may be performed as described in U.S. Pat. No. 5,720,291, and in U.S. Pat. Nos. 5,474,073 and 5,485,842, all of which are incorporated herein by reference.

The signals from the contrast signal processor 38, the B mode processor 36 and the Doppler processor 40, and the three dimensional image signals from the 3D image memory 44 are coupled to a Cineloop® memory 48, which stores image data for each of a large number of ultrasonic images. The image data are preferably stored in the Cineloop memory 48 in sets, with each set of image data corresponding to an image obtained at a respective time. The image data in a group can be used to display a parametric image showing tissue perfusion at a respective time during the heartbeat. The groups of image data stored in the Cineloop memory 48 may also be stored in a permanent memory device such as a disk drive or digital video recorder for later analysis. In this embodiment the images are also coupled to a QLAB processor 50, where the images are analyzed to automatically delineate borders of the heart, enabling a user to then position a border as the user believes most accurately indicates the true border of a chamber of the heart. The QLAB processor also makes quantified measurements of various aspects of the anatomy in the image and delineates tissue boundaries and borders by automated border tracing as described in US patent publication no. 2005/0075567 and PCT publication no. 2005/054898. The data and images produced by the QLAB processor are displayed on a display 52.

Figure 2:
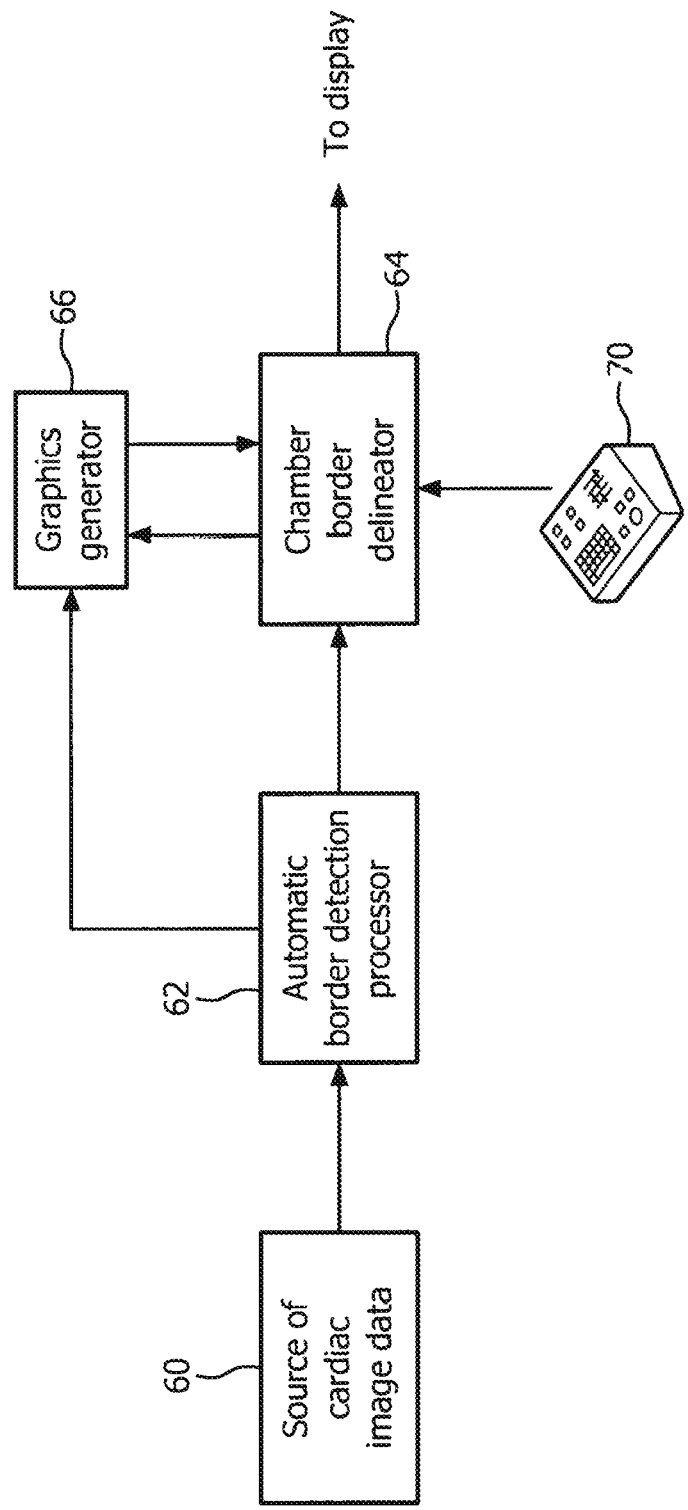
FIG. 2 is a block diagram illustrating border detection details of the QLQB processor of FIG. 1 in accordance with the principles of the present invention.
Figure 3B:
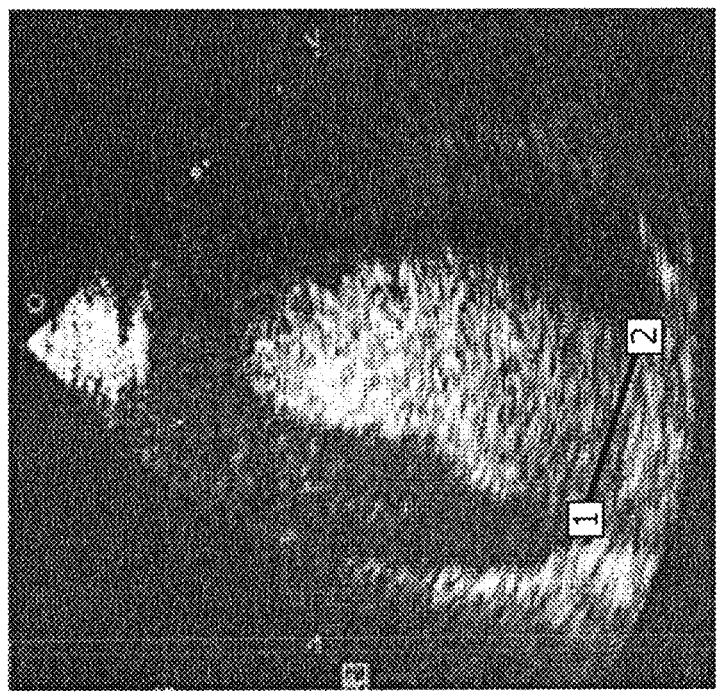
FIGS. 3a and 3b illustrate landmarks of the left ventricle which are useful for border detection.
Figure 3A:
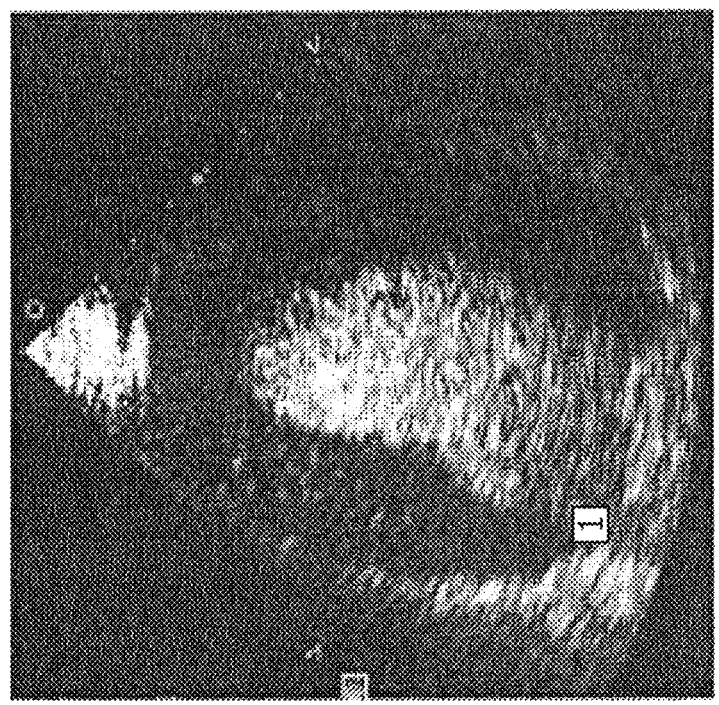
Figure 4C:
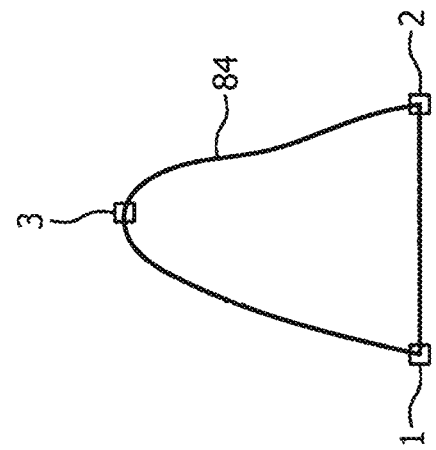
FIGS. 4a, 4b and 4c illustrate expert-derived endocardial border shapes used for automated border detection.
Figure 4B:
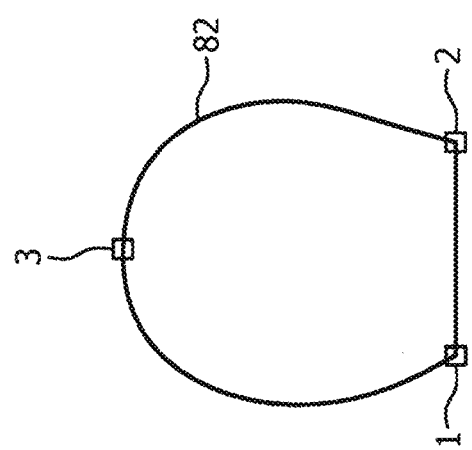
Figure 4A:
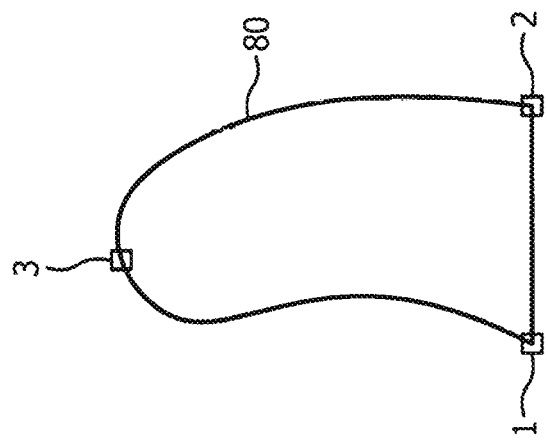
Figure 5B:
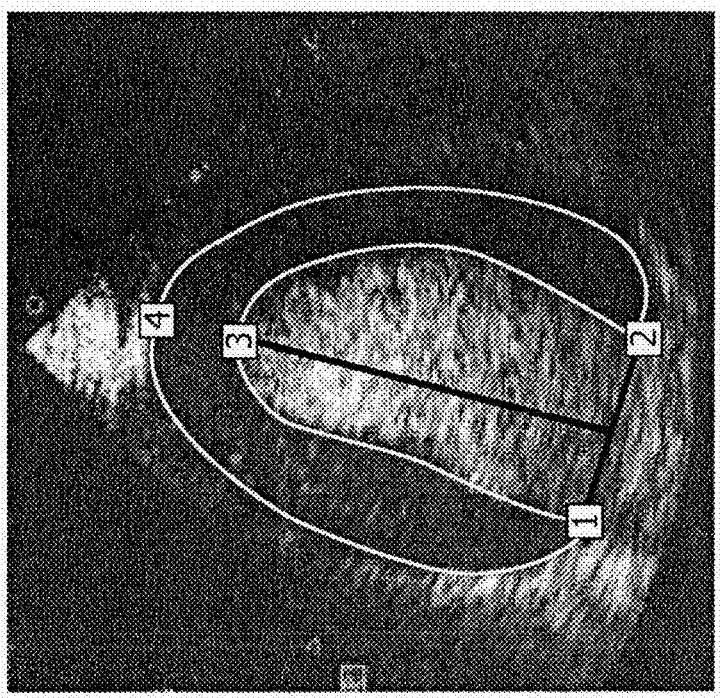
FIGS. 5a and 5b illustrates the delineation of epicardial and endocardial borders in images of the left ventricle.
Figure 5A:
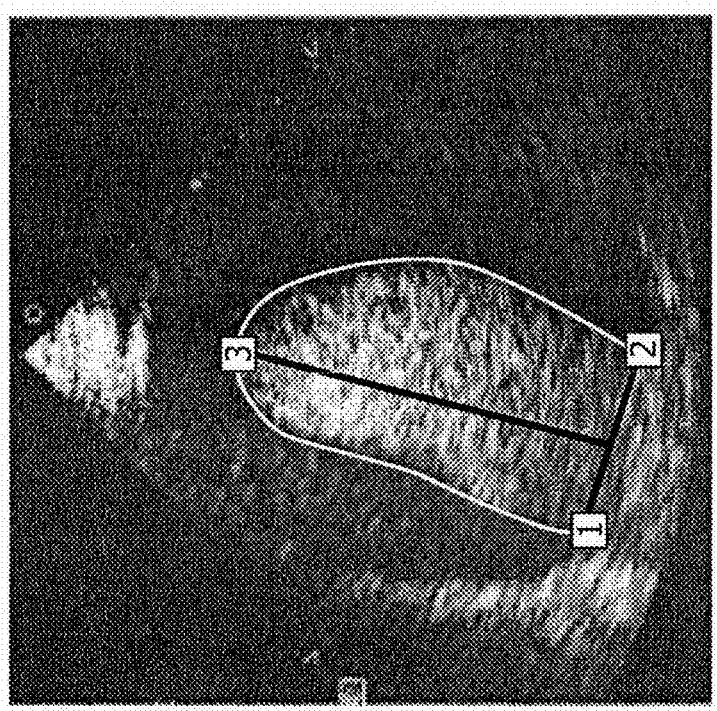

FIG. 2 illustrates further details of the operation of the QLAB processor to delineate a user-defined heart chamber border in accordance with the principles of the present invention. A cardiac ultrasound image is provided by a source of cardiac image data 60, which may be the Cineloop memory 48, the 3D image memory 44, or one of image processors 36, 38, or 40 of FIG. 1. The cardiac image is forwarded to an automatic border detection (ABD) processor 62. The ABD processor may be a fully automatic or a semi-automatic (user-assisted) image processor which delineates a border of a chamber in a heart image, several of which are described below. In a typical semi-automatic ABD system, the user designates a first landmark in the cardiac image with a pointing device such as a mouse or a trackball, usually located on the ultrasound system control panel 70 or with a workstation keyboard, which manipulates a cursor over the image. In the example of FIG. 3a, for instance, the first landmark designated is the medial mitral annulus (MMA) at the bottom of the left ventricle (LV) in the illustrated view. When the user clicks on the MMA in the image, a graphic marker appears such as the white control point indicated by the number "1" in the drawing. The user then designates a second landmark, in this example, the lateral mitral annulus (LMA), which is marked with the second white control point indicated by the number "2" in FIG. 3b. A line produced by the ABD processor then automatically connects the two control points, which in the case of this longitudinal view of the left ventricle indicates the mitral valve plane. The user then moves the pointer to the endocardial apex, which is the uppermost point within the left ventricular cavity. As the user moves the pointer to this third landmark in the image, a template shape of the left ventricular endocardial cavity dynamically follows the cursor, distorting and stretching as the user-manipulated pointer seeks the apex of the LV chamber, as shown in FIG. 5a. This template, shown as a white line in FIG. 5a, is anchored by the first and second control points 1 and 2 and passes through the third control point, which is positioned at the apex when the user clicks the pointer at the apex, positioning the third control point 3. Typical LV chamber border templates are shown in FIGS. 4a, 4b, and 4c. These templates are determined from many expert tracings of the LV endocardial boundary in many patients. The template 80 of FIG. 4a is an elongated template typical of many normal patients. The template 82 of FIG. 4b is more bulbous in shape, characteristic of many patients with congestive heart failure. The template 84 is yet a third possibility, a more teardrop shape. The template which best fits the three anatomical landmarks identified by the user is selected by the ABD processor 62 and distorted to fit the three user-defined landmarks. When positioned and fitted to the landmarks, the endocardial cavity template 80, 82, or 84 provides an approximate tracing of the endocardium of the LV, as shown in FIG. 5a. In the example of FIG. 5a a black line which bisects the left ventricle follows the pointer as it approaches and designates the apex. This black line is anchored between the center of the line indicating the mitral valve plane and the left ventricular apex, essentially indicating a center line between the center of the mitral valve and the apex of the cavity.

Once the ABD processor 62 has found the endocardial lining of the LV, it then attempts to find the epicardial boundary. This is illustrated in FIG. 5b, where the user has moved the cursor and clicked on the apex 4 of the outside of the dark myocardium in the image. The images of FIG. 5 are contrast-enhanced harmonic images in which the chamber of the LV has been flooded with a contrast agent but the agent has not yet fully perfused the myocardium, which is why the LV chamber appears very bright against the darker surrounding myocardium in this image. When the user clicks on the epicardial apex, the ABD processor, as before, selects an outer or epicardial template similar to the templates of FIG. 4 and fits it to the epicardium as illustrated in FIG. 5b. The cardiac image now has both its endocardial boundary (line connecting 1, 3 and 2 markers), the blood pool-myocardium interface, and its epicardial boundary (line connecting 1, 4 and 2 markers), the outmost surface of the heart, delineated in the image by tracings produced by a graphics generator 66.

Figure 6:
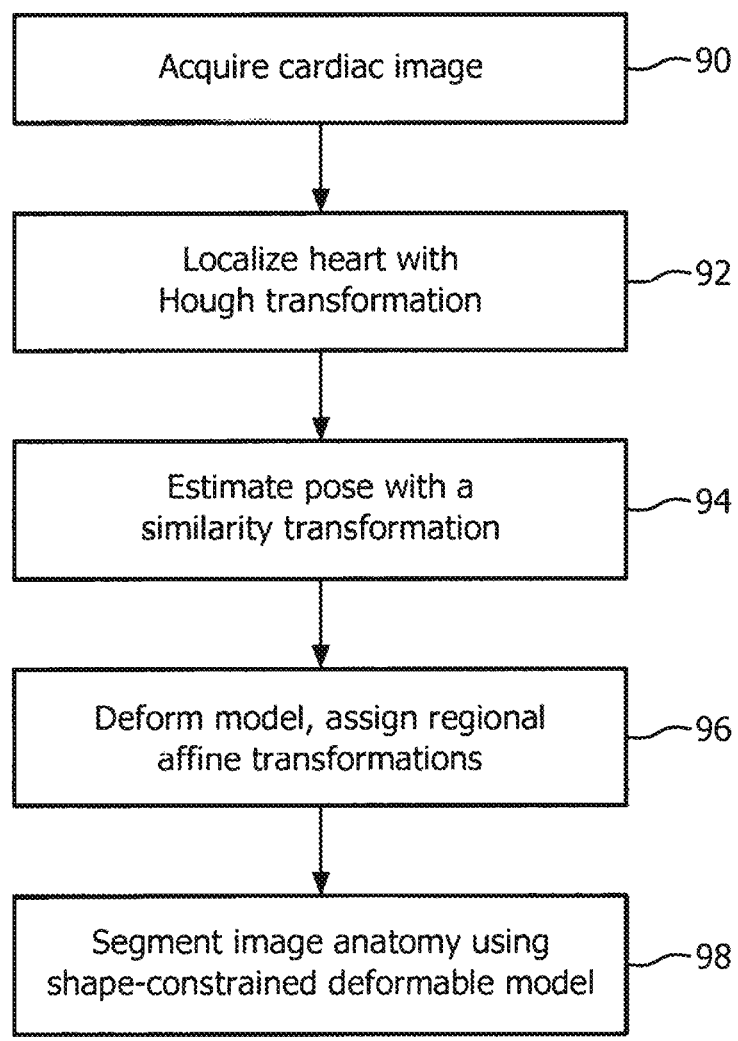
FIG. 6 is a flowchart of the operation of a deformable heart model to find heart borders in accordance with the present invention.

Instead of semi-automatic operation requiring user interaction, the ABD processor may delineate the border of the LV fully automatically as described in the aforementioned U.S. Pat. No. 6,491,636. As explained therein, an image processor can be configured to find the mitral valve corners and apex automatically, then fit a template to the automatically-located landmarks. However, a preferred technique for automatically delineating the myocardial borders is with a deformable heart model, as illustrated in FIG. 6. A heart model is a spatially-defined mathematical description of the tissue structure of a typical heart which can be fitted to the heart as it appears in a diagnostic image, thereby defining the specific anatomy of the imaged heart. Unlike a standard heart model designed to identify interior structures of the heart such as valves and chambers, the heart model of the present invention is designed to locate multiple myocardial boundaries, including both an inner endocardial boundary and an outer interface between the trabeculated myocardium and the compacted myocardium. The process of FIG. 6 begins with the acquisition of a cardiac image at 90. The position of the heart is then localized in the cardiac image by processing the image data with a generalized Hough transform at 92. At this point the pose of the heart has not been defined, so misalignments in translation, rotation and scaling of the heart in the image data are corrected by use of a single similarity transformation for the whole heart model at 94. Next at 96, the model is deformed and affine transformations are assigned to specific regions of the heart. Constraints on the deformation are then relaxed by allowing the heart model to deform with respect to the piecewise affine transformation at 98, and the shape-constrained deformable model is resized and deformed so that each part of the model fits the actual patient anatomy as shown in the image at the captured phase of the heart cycle, including both an inner and outer myocardial boundaries. The model is thus accurately adapted to the organ boundaries shown in the cardiac image, thereby defining the boundaries including the endocardial lining, the interface between the trabeculated myocardium and the compacted myocardium, and the epicardial border. In a preferred implementation of such a heart model, the interface between the trabeculated myocardium and the compacted myocardium is found first, as this typically appears as a well-defined gradient between a brightly illuminated region and a region of moderate illumination in an ultrasound image. The endocardial boundary is generally less well-defined in a heart model due to the desire to be able to find the variable location of the less well-defined endothelial lining as it appears in an ultrasound image. Unlike the contrast-enhanced cardiac images of FIGS. 5a and 5b, an unenhanced ultrasound image will generally exhibit a relatively sharp intensity gradient between the relatively high intensity echo tissue surrounding the myocardium and the medium intensity of the myocardium, and a relatively lesser gradient between the myocardium and the low intensity of the chamber's blood pool. This mandates in favor of discriminating the outer myocardial border first, then the inner endocardial boundary when diagnosing images acquired in the absence of a contrast agent. When the coordinates of a boundary have been found, they are communicated to the graphics generator 66, which generates the traces that overlie the image in the calculated positions.

Figure 7A:
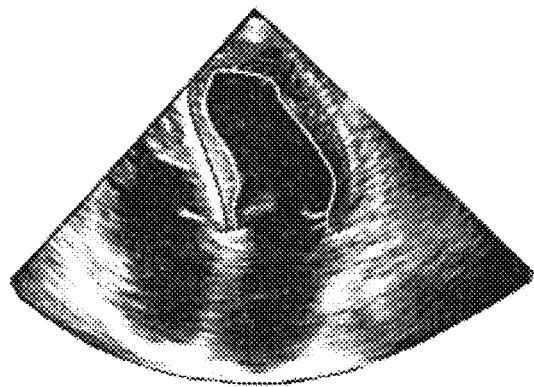
FIGS. 7a and 7b are cardiac images of the left ventricle at end diastole and end systole in which the endocardial boundary and the interface between the trabeculated myocardium and the compacted myocardium have been traced.
Figure 7B:
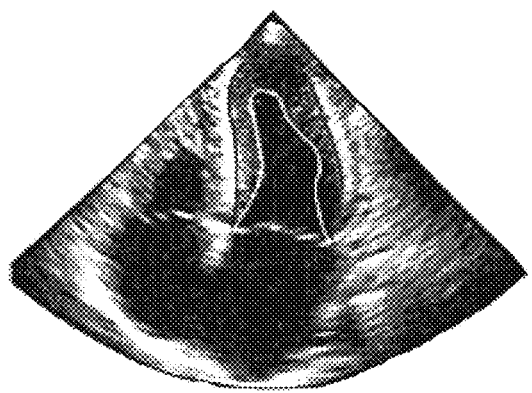
Figure 8A:
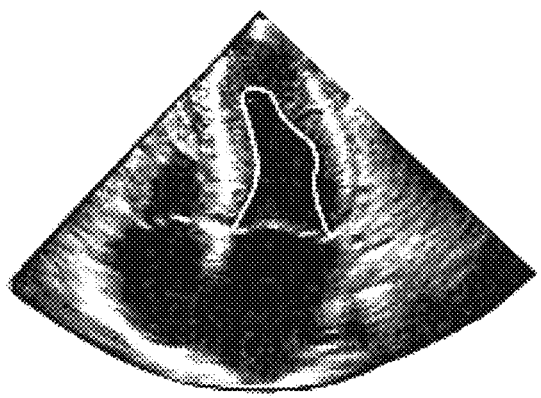
FIGS. 8a and 8b illustrate the end systole ultrasound image of FIG. 7b in which a user-defined border has been located at 0% and 100% of the distance between the two heart boundaries delineated in FIG. 7b.
Figure 8B:
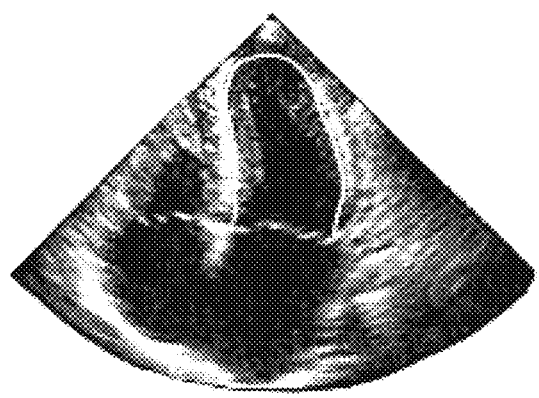

FIG. 7 shows two ultrasound images, one with both boundaries of the myocardium outlined at end diastole (FIG. 7a), and the second with both myocardial boundaries traced at end systole (FIG. 7b). The compacted myocardial boundary is traced in black and the endocardial boundary is traced in white in these images. With both boundaries thus identified by use of the heart model, the user controls a chamber border delineator 64 with a user control on control panel 70 to indicate a location between the two myocardial tracings where the user believes the true chamber border is located. In one implementation the user operates a single variable control by which the user can position the true endocardial border at a location which is displaced a selected percentage of the distance between the previously drawn endocardial boundary and the previously drawn interface between the trabeculated myocardium and the compacted myocardium. FIG. 8a illustrates the end systole image of FIG. 7b when the single variable control is set at 0%, and FIG. 8b illustrates the same image with the user control set at 100%, in which case the white line border is located at the outside of the myocardium. The visual tracing of the user-defined border is also produced by the graphics generator 66 in the system of FIG. 1 for overlay over the ultrasound image. The user-set border is positioned at the called-for location as measured orthogonal to the endocardial tracing and at the called-for percentage of the distance between the two boundaries. In these examples the two myocardial boundary tracings are not shown for ease of illustration, which is one possible implementation, although the automatically drawn tracings could also be shown if desired.

Figure 8C:
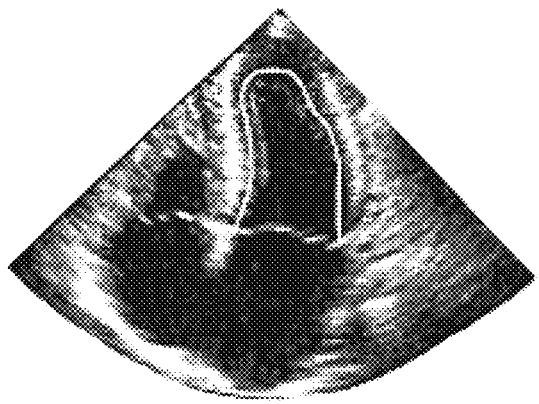
FIG. 8c illustrates a cardiac image with a user-defined border is located at 40% of the distance toward the compacted myocardium interface from the endocardial tracing.

FIG. 8c illustrates a situation in which the user has adjusted the user-positioned border (shown as a white line) so that it is 40% of the distance toward the epicardial or compacted myocardium interface from the endocardial tracing. This is done by moving a slider 100 left or right in its slot 102. As the slider is manipulated by the user, the user-controlled border tracing 110 moves back and forth between the two boundaries of the myocardium. In the example of FIG. 8c the slider 100 is shown as a softkey control on the display screen which is manipulated by a mouse or other user interface control, although the slide could alternatively be a physical slider, knob or switch, or a trackball on a conventional ultrasound system control panel. The user control can also be implemented as a rocker control, toggle buttons, list box, or a numerical entry box. If the user has a preferred percentage for most cases, this can be saved as a default value. In the example of FIG. 8c the numerical percentage is displayed on the screen and changes as the slider 100 is moved. Also shown in FIG. 8d in an enlarged view 104 of a portion of the traced boundaries. The user clicks on a point of the myocardium of the image to the left, and that portion of the myocardium appears in the enlarged view 104, with the user-manipulated border 110 shown between the myocardial boundaries 106 (outer boundary) and 108 (inner boundary). As the user manipulates the slider 100, the border 110 moves between the two system-drawn boundaries 106 and 108. The user-manipulated border 110 can also be positioned using a range of more than 100% as shown in the enlarged view 104'. The user-defined position A (110'A) is positioned beyond the compacted myocardium boundary 106' and expressed in the range of more than 100%, while the user-defined position C (110'C) is positioned within the endocardial tracing 108' and expressed in negative percentage range. The user-defined position B (110'B) positioned in between the endocardial and compacted myocardium boundaries can be expressed in the range in between 0% and 100%.

Figure 8D:
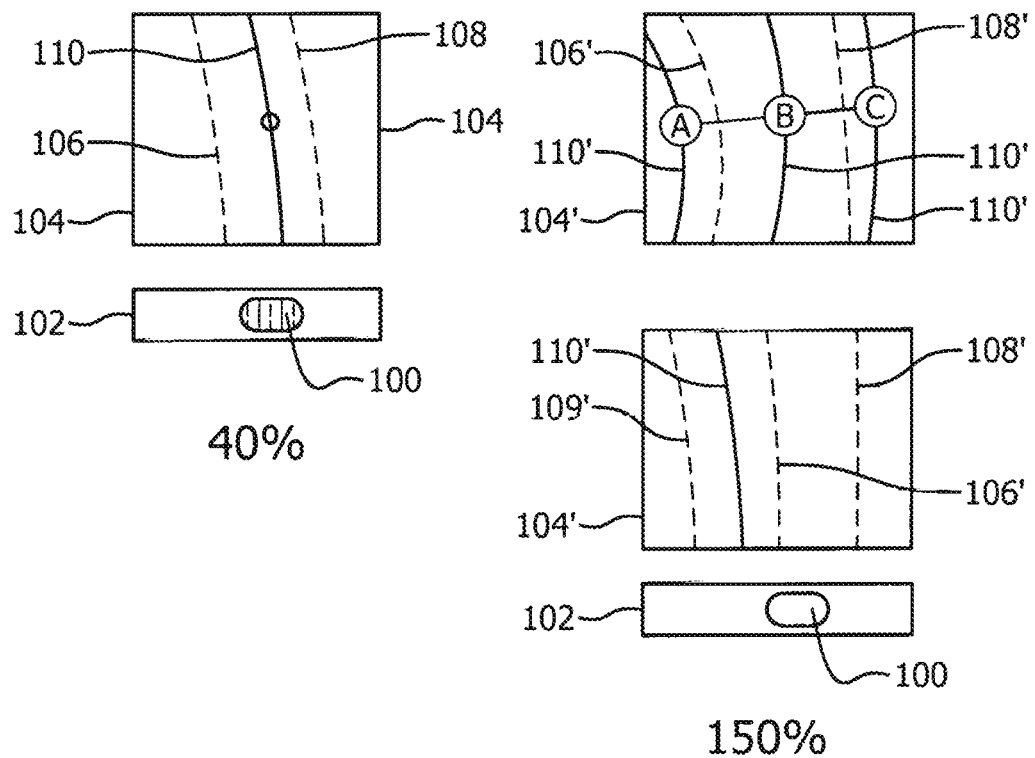
FIG. 8d illustrates a single degree of freedom user control in accordance with the embodiments of the present invention, wherein the user-defined border is located relative to several boundaries of the myocardium.

Alternatively, for user convenience the user-manipulated (defined) border can be moved with respect to three outlines as illustrated in FIG. 8d (lower to the right view 104'): the compacted myocardium boundary 106' and endocardial boundary 108', which correspond to the same percentage 100% and 0% respectively as in the previous example; and an additional boundary 109' corresponding to the percentage value of 200%, wherein the additional boundary 109' is located at the epicardial boundary. In the illustrated example, the slider 100 is adjusted at the value of 150% corresponding to the user-defined border 110' position in between the compacted myocardium boundary 106' and the epicardial boundary 109'. The alternative of the third boundary is addressing the fact that there is another boundary beyond the compacted myocardium boundary (106'), which is the epicardial boundary (denoted in this example as the additional boundary), said epicardial boundary may be also characterized by a noticeable and detectable gradient in the ultrasound image, which could be used to constrain the single degree of freedom slider. This epicardial boundary can be also identified by the border image processor.

The slider is a single degree of freedom control. The user sets the position of the border 110 all around the chamber simply by setting the single value controlled by the slider. The value can be communicated to other users, who can obtain the same results by use of the same single numerical value.

Figure 9:
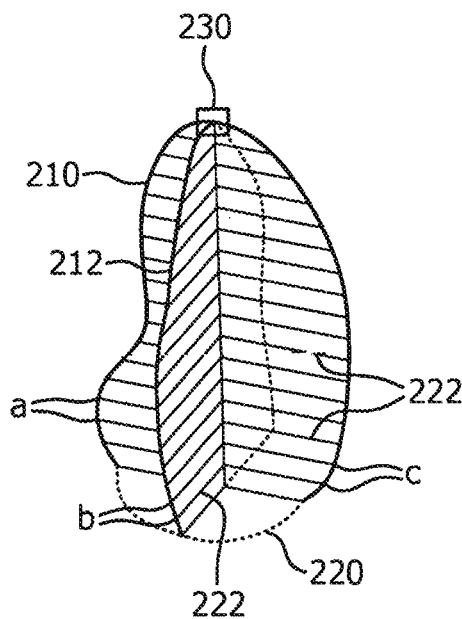
FIG. 9 illustrates user-defined heart chambers from biplane images which are being volumetrically measured using the rule of disks.
Figure 10:
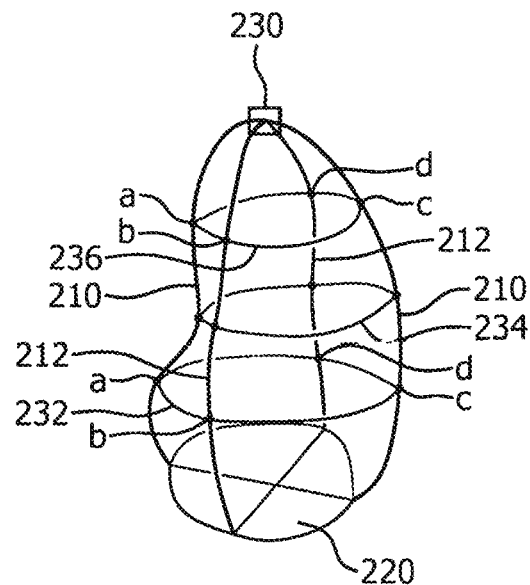
FIG. 10 illustrates a user-defined heart chamber wire frame model from a 3D ultrasound image preparatory to volumetric measurement.

FIGS. 9 and 10 illustrate how user-defined heart chamber borders of the present invention can be used to measure parameters such as cardiac output and ejection fraction. In the perspective view of FIG. 9 two user-defined borders 210 and 212 of simultaneously acquired biplane images of the LV are shown on a base 220 which represents the mitral valve plane. The apex marker of the two borders is shown at 230. In this example the image planes of the two biplane image borders are orthogonal to each other. The volume within the two borders 210 and 212 is mathematically divided into spaced planes 222 which are parallel to the base plane 220. These planes intersect the left side of border 210 as shown at a,a and intersect the right side of border 210 as shown at c,c. The planes intersect the near side of tracing 212 as shown at b,b.

An ellipse is mathematically fit to the four intersection points a,b,c,d of each plane 222 as shown in FIG. 9. While curves or splines other than ellipses can be used, including arcs and irregular shapes, an ellipse provides the advantage that Simpson's formula has been clinically validated when practiced with ellipses. The volume of the disks defined by the planes 222 and the ellipses can be calculated by the rule of disks to estimate the volume of the LV.

FIG. 10 shows a wire frame model constructed of a user-defined border of a three dimensional heart chamber image. The horizontal sections 232, 234, 236 of the wire frame are border lines which intersect vertical border sections 210, 212 at intersection points a, b, c, and d. The horizontal sections are parallel to the mitral valve plane base 220. The volume within the wire frame can be determined by a modified rule of disks computation or other volumetric estimation technique. When a volume computed as shown in FIG. 9 or 10 for an end systole phase image is subtracted from a volume calculated for an end diastole image and divided by the same, the result is an ejection fraction estimation.

Other variations of the above will readily occur to those skilled in the art. Instead of a percentage quantification, the user-defined border can be positioned an incremental distance from a manual or automatically traced boundary. The slider can be calibrated in distance so that the position of a user-defined border is a user-determined number of millimeters offset from a reference boundary, for instance. Rather than use two traced boundaries, the user-defined border can be located in reference to a single boundary tracing, or can be at an interpolated offset from more than two boundaries.

The invention claimed is:

1. An ultrasonic diagnostic imaging system for determining the border of a chamber of the heart in an ultrasound image comprising:
   a source of cardiac image data;
   a border detection processor that receives the cardiac image data and comprises a deformable heart model configured to identify at least an inner boundary and an outer boundary of a myocardium in the cardiac image data;
   a chamber border delineator coupled to the border detection processor, wherein the chamber border delineator causes to be displayed a display trace of a user-defined border of a heart chamber in the cardiac image data, wherein the user-defined border is distinct from the inner boundary and the outer boundary identified by the border detection processor; and a user control that enables the user to adjust a location of the user-defined border by adjusting a location of the user-defined border as a function of a distance between the inner boundary and the outer boundary.

2. The ultrasonic diagnostic imaging system of claim 1, wherein the function of the distance between the inner boundary and the outer boundary is a percentage displacement of the location of the user-defined border relative to the inner boundary and the outer boundary.

3. The ultrasonic diagnostic imaging system of claim 2, wherein the deformable heart model is further configured to identify in the cardiac image data an endocardium or a myocardium-blood pool interface as the inner boundary, and
an epicardium or an interface between the trabeculated myocardium and the compacted myocardium as the outer boundary.

4. The ultrasonic diagnostic imaging system of claim 2, wherein the user control further comprises a slider, a knob, a switch, a trackball, a rocker control, toggle buttons, a list box, a numerical entry box, a softkey control, or a physical control.

5. The ultrasonic diagnostic imaging system of claim 2, wherein the percentage displacement is zero when the location of the user-defined border coincides with the inner boundary, wherein the percentage displacement is one hundred when the location of the user-defined border coincides with the outer boundary.

6. The ultrasonic diagnostic imaging system of claim 5, wherein the percentage displacement is less than zero when the location of the user-defined border is within the inner boundary and the percentage displacement is greater than one hundred when the location of the user-defined border is beyond the outer boundary.

7. The ultrasonic diagnostic imaging system of claim 1, wherein the source of cardiac image data further comprises a memory device containing two-dimensional cardiac images.

8. The ultrasonic diagnostic imaging system of claim 7, wherein the source of cardiac image data is adapted to provide the border detection processor with two-dimensional cardiac images including a view of a left ventricle.

9. The ultrasonic diagnostic imaging system of claim 1, wherein the deformable heart model is further configured to initially localize the position of the heart in the image data with a generalized Hough transform.

10. The ultrasonic diagnostic imaging system of claim 9, wherein the deformable heart model is further configured to determine the pose of the heart in the image data by use of a single similarity transformation.

11. The ultrasonic diagnostic imaging system of claim 10, wherein the deformable heart model is further configured to deform with respect to piecewise affine transformations.

12. The ultrasonic diagnostic imaging system of claim 1, further comprising a graphics generator, coupled to the boundaries identified by the heart model, which is arranged to produce display traces of the inner and outer boundaries; and
a display, coupled to the source of cardiac image data and to the graphics generator, which is arranged to display a cardiac image with the display traces of the inner and outer boundaries.

13. The ultrasonic diagnostic imaging system of claim 1, further comprising a graphics generator, coupled to the chamber border delineator, which is arranged to produce the display trace of the user-defined border; and
a display, coupled to the source of cardiac image data and to the graphics generator, which is arranged to display a cardiac image with the display trace of the user-defined border.

14. The ultrasonic diagnostic imaging system of claim 2, wherein the percentage displacement is based on a distance of the location of the user-defined border from the inner boundary along a direction orthogonal to the inner boundary and a distance from the outer boundary to the inner boundary along said direction.

15. The ultrasonic imaging system of claim 1, wherein the deformable heart model is configured to:
identify an interface between a trabeculated myocardium and a compacted myocardium;
identify the outer boundary after the interface has been identified; and
identify the inner boundary after the outer boundary has been identified.

16. The ultrasonic imaging system of claim 6, wherein the outer boundary is a compacted myocardium boundary of the myocardium and the inner boundary of the myocardium is an endocardial boundary of the myocardium, wherein the deformable heart model is further configured to identify an additional boundary, wherein the additional boundary is an epicardial boundary.

17. The ultrasonic imaging system of claim 16, wherein the additional boundary constrains a range of the percentage displacement.

18. The ultrasonic imaging system of claim 1, further comprising a processor configured to:
generate a wire frame model of a three dimensional heart chamber based on the user-defined border; and
determine a volume of the three dimensional heart chamber based on a modified rule of disks computation.

19. The ultrasonic imaging system of claim 18, wherein the processor is further configured to:
determine a first volume of the three dimensional heart chamber at end systole;
determine a second volume of the three dimensional heart chamber at end diastole; and
subtract the first volume from the second volume to generate an ejection fraction estimation.

\* \* \* \* \*